(12) United States Patent
Wasowski (10) Patent No.: US 10,357,421 B2
(45) Date of Patent: Jul. 23, 2019

(54) APPARATUS AND METHOD FOR ENHANCED HGH GENERATION IN HUMANS

(75) Inventor: Peter Z. Wasowski, Los Gatos, CA (US)

(73) Assignee: Vasper Systems, LLC, Moffett Field, CA (US)

( * ) Notice: Subject to any disclaimer, the term of this patent is extended or adjusted under 35 U.S.C. 154(b) by 1273 days.

(21) Appl. No.: 13/094,799

(22) Filed: Apr. 26, 2011

(65) Prior Publication Data

US 2012/0277641 A1 Nov. 1, 2012

(51) Int. Cl.
*A61F 7/00* (2006.01)
*A61F 5/34* (2006.01)
(Continued)

(52) U.S. Cl.
CPC .............. *A61H 9/0078* (2013.01); *B64G 1/60* (2013.01); *B64G 1/66* (2013.01); *A61F 2007/0002* (2013.01); *A61F 2007/0024* (2013.01); *A61F 2007/0029* (2013.01); *A61F 2007/0039* (2013.01); *A61F 2007/0056* (2013.01); *A61F 2007/0091* (2013.01); *A61F 2007/0093* (2013.01); *A61H 2201/0214* (2013.01); *A61H 2201/0264* (2013.01); *A61H 2201/5071* (2013.01); *A61H 2203/0456* (2013.01); *A61H 2205/02* (2013.01); *A61H 2205/06* (2013.01);
(Continued)

(58) Field of Classification Search
CPC ............ A61H 9/0078; A61H 2201/165; A61H 2201/0214; A61H 2201/0242; A61F 2007/0054; A61F 2007/0056; A61F 7/00; A61F 7/0085; A61F 2007/0001; A47C 21/04; A47C 21/042; A47C 21/044

USPC ..... 600/16, 17; 601/148–152; 606/201, 202; 607/96, 104
See application file for complete search history.

(56) References Cited

U.S. PATENT DOCUMENTS 1,970,200 A * 8/1934 Short ................... A61F 7/02 165/175
2,260,134 A * 10/1941 Ballman ............... A61F 7/02 126/210
(Continued)

FOREIGN PATENT DOCUMENTS

WO WO 2007/056130 5/2007

OTHER PUBLICATIONS

"Your Target Heart Rate." Your Best Training Tool. N.p., Mar. 1, 2009. Web. Aug. 14, 2015.*
(Continued)

*Primary Examiner* — Michael J Tsai
*Assistant Examiner* — Christopher E Miller
(74) *Attorney, Agent, or Firm* — Jay A. Chesavage; File-EE-Patents.com (57) ABSTRACT

A conditioning process for the enhanced production of human growth hormone in a human has a first step of application of pressurized cooling to the limbs of a subject, who experiences a ramp-up exertion followed by a series of conditioning cycles, followed by a ramp-down cycle. The condition cycles include an interval of intense exertion followed by an interval of reduced exertion, and during ramp-up cycle, conditioning cycle, and ramp-down cycle, the pressure cooling to the limbs is set as a fraction of systolic blood pressure, with the fraction in the range 33% to 220%.

22 Claims, 7 Drawing Sheets

(51) Int. Cl.
*A61H 9/00* (2006.01)
*B64G 1/60* (2006.01)
*B64G 1/66* (2006.01)

(52) U.S. Cl.
CPC .... *A61H 2205/10* (2013.01); *A61H 2230/255* (2013.01); *A63B 2213/006* (2013.01); *A63B 2225/66* (2013.01)

(56) References Cited

U.S. PATENT DOCUMENTS

| | | | | |
|---|---|---|---|---|
| 4,132,262 | A * | 1/1979 | Wibell | A47G 9/0215 165/206 |
| 4,149,529 | A * | 4/1979 | Copeland et al. | 601/17 |
| 4,479,494 | A * | 10/1984 | McEwen | A61B 5/02141 600/495 |
| 4,691,762 | A * | 9/1987 | Elkins et al. | 165/46 |
| 4,738,119 | A * | 4/1988 | Zafred | A41D 13/0053 2/81 |
| 4,844,072 | A | 7/1989 | French et al. | |
| 4,884,304 | A * | 12/1989 | Elkins | 5/421 |
| 4,979,375 | A * | 12/1990 | Nathans | A47C 1/143 5/422 |
| 5,080,089 | A | 1/1992 | Mason et al. | |
| 5,433,741 | A * | 7/1995 | Truglio | A61F 7/02 128/870 |
| 5,571,075 | A * | 11/1996 | Bullard | 601/152 |
| 5,683,438 | A * | 11/1997 | Grahn | A61F 7/02 126/204 |
| 5,785,716 | A * | 7/1998 | Bayron | A61F 7/00 126/204 |
| 5,803,870 | A * | 9/1998 | Buhler | 482/8 |
| 5,879,270 | A * | 3/1999 | Huish et al. | 482/8 |
| 5,966,763 | A * | 10/1999 | Thomas | A47C 27/086 5/421 |
| 6,113,626 | A * | 9/2000 | Clifton | A61F 7/0097 607/104 |
| 6,273,810 | B1 * | 8/2001 | Rhodes, Jr. | A47C 4/54 297/180.13 |
| 6,336,907 | B1 * | 1/2002 | Dono et al. | 601/150 |
| 6,565,699 | B1 * | 5/2003 | Szczesuil | A41D 13/005 156/290 |
| 6,606,754 | B1 * | 8/2003 | Flick | A47C 21/044 5/421 |
| 7,089,995 | B2 * | 8/2006 | Koscheyev | A41D 13/005 165/46 |
| 8,182,520 | B2 * | 5/2012 | Schock | A61F 7/00 607/104 |
| 8,523,927 | B2 * | 9/2013 | Levinson et al. | 607/96 |
| 8,544,115 | B1 * | 10/2013 | Gravenstein | A42B 3/285 2/81 |
| 8,585,746 | B2 * | 11/2013 | Ilcheva | A41D 13/005 607/108 |
| 2002/0032473 | A1 * | 3/2002 | Kushnir et al. | 607/104 |
| 2002/0107558 | A1 * | 8/2002 | Clifton | A61F 7/02 607/104 |
| 2003/0046762 | A1 * | 3/2003 | Stolpmann | A61F 7/00 5/421 |
| 2003/0097163 | A1 * | 5/2003 | Kane et al. | 607/108 |
| 2005/0026750 | A1 * | 2/2005 | Oglesby et al. | 482/8 |
| 2005/0070405 | A1 | 3/2005 | Egger | |
| 2005/0103353 | A1 * | 5/2005 | Grahn | A61F 7/02 128/898 |
| 2005/0126578 | A1 | 6/2005 | Garrison | |
| 2005/0143797 | A1 * | 6/2005 | Parish et al. | 607/104 |
| 2005/0211192 | A1 * | 9/2005 | Nilforushan | A01K 13/006 119/850 |
| 2006/0111765 | A1 * | 5/2006 | Kirkman, Jr. | 607/104 |
| 2006/0191675 | A1 * | 8/2006 | Fletcher | F28F 3/022 165/172 |
| 2006/0276089 | A1 * | 12/2006 | Amarasinghe | A41D 13/0053 442/121 |
| 2006/0276552 | A1 * | 12/2006 | Barbut | A61F 7/12 514/743 |
| 2007/0135878 | A1 * | 6/2007 | Lachenbruch | A61G 7/057 607/108 |
| 2008/0040839 | A1 * | 2/2008 | Gordon | A41D 13/0053 2/455 |
| 2008/0234788 | A1 * | 9/2008 | Wasowski | 607/104 |
| 2009/0108082 | A1 * | 4/2009 | Goldmann | F24F 11/0012 236/49.1 |
| 2009/0247809 | A1 | 10/2009 | Loeb et al. | |
| 2009/0287243 | A1 * | 11/2009 | Greennberg | A61H 9/0078 606/202 |
| 2009/0287281 | A1 * | 11/2009 | Munson | 607/104 |
| 2009/0312823 | A1 * | 12/2009 | Patience | A61F 7/007 607/104 |
| 2010/0198319 | A1 * | 8/2010 | Arad | A61F 7/12 607/105 |
| 2010/0292619 | A1 * | 11/2010 | Redington et al. | 601/84 |
| 2010/0298723 | A1 * | 11/2010 | Zhen | 600/490 |
| 2011/0022137 | A1 * | 1/2011 | Ennis-Thomas et al. | 607/108 |
| 2011/0065371 | A1 * | 3/2011 | Leff | F24F 1/0007 454/237 |
| 2011/0107514 | A1 * | 5/2011 | Brykalski | A47C 21/044 5/421 |
| 2011/0115635 | A1 * | 5/2011 | Petrovski | A47C 21/044 340/584 |
| 2011/0152982 | A1 * | 6/2011 | Richardson | 607/104 |
| 2011/0319732 | A1 * | 12/2011 | Naghavi et al. | 600/335 |
| 2012/0158103 | A1 * | 6/2012 | Bledsoe | A61F 7/02 607/104 |

OTHER PUBLICATIONS

PCT Application No. PCT/US2012/035069, filed Apr. 26, 2012, International Search Report dated Aug. 13, 2012.
Wahl et al., Effect of High and Low Intensity Exercise Metabolic Acidosis on levels GH IGF-I, IGFBP-3 and Cortisol. Growth Hormone and IGF Research, 20:380-385, Aug. 30, 2010.
Human Growth Hormone in Your Body Can Transform Your Health—Takes Just 20 Minutes, "How to Properly Perform Sprint 8 to Increase Your Growth Hormone Levels", http://fitness.mercola.com/sites/fitness/archive/2010/12/24/a-fountain-of-youth-in-your-muscles.aspx Dec. 24, 2010.
Peter Z. Wasowski, Entitled Singapore Application No. 2013079520, "Apparatus and Method for Enhanced HGH Generation in Humans" International Filing Date: Apr. 26, 2012, Examination Report dated Nov. 24, 2014.
Peter Z. Wasowski, European Application No. 12777729.0, Entitled "Apparatus and Method for Enhanced HGH Generation in Humans" International Filing Date: Apr. 26, 2012, Extended Search Report dated Dec. 10, 2014.
Peter Z. Wasowski, Singapore Application No. 2013079520, Entitled "Apparatus and Method for Enhanced HGH Generation in Humans" International Filing Date: Apr. 26, 2012, Examination Report dated May 12, 2015.
Bobby Curran. Vasper Gets You Moving Again Whole document, Mar. 30, 2011.
PCT Application No. PCT/US2012/035069, filed Apr. 26, 2012, International Preliminary Exam Report dated Nov. 7, 2013.

* cited by examiner

Figure 2A
Conditioning Process

*Figure 2B*
Conditioning Process

*Figure 2C*
Conditioning Process

Fig 4B Gravity Closure
Fig 4C Muscle Assist
1G standing

Fig 4D
0G space
Retrograde flow

Fig 4E
0G space
Cuff Assist

Fig 4F
0G space
Cuff Assist

Fig 4G
sequentially inflating cuff

Figure 7
Cooling Mat with Temperature Profile

Figure 7A
Temperature Profile

APPARATUS AND METHOD FOR ENHANCED HGH GENERATION IN HUMANS

FIELD OF THE INVENTION

The present invention relates to a physical conditioning method for use with an exercise apparatus. In particular, the present invention relates to a conditioning method for enhancement of human growth hormone (HGH).

BACKGROUND OF THE INVENTION

One prior art method of increasing muscle mass uses low-intensity resistance training where a relatively light and flexible cuff or elastic band is placed on the proximal part of a subject's lower or upper limbs, and the cuff or band provides sufficient constriction of the limb to reduce blood flow. The resultant reduction of blood flow generates blood pooling in the capillaries of the muscles opposite the blood flow constriction with relation to the heart. The article "Effects of resistance exercise combined with moderate vascular occlusion on muscular function in humans" in J Appl Physiol 88: 2097-2106, 2000 by Takarada teaches muscle bulk enhancement by light exercise in combination with vascular occlusion. One exemplar system which provides this occlusion is the KAATSU system of Sato, described in U.S. Patent application 2006/0281611 and Japan Patent application published as PCT/JP2003/016163, and U.S. Pat. No. 7,413,527. In this system, a constricting band is placed around a limb that is being physically conditioned to increase lactic acid buildup. Long term exertion which is at or below the capillary blood oxygen replacement rate is known as aerobic exercise, and short term exertion which is above muscle capillary oxygen replacement rate is known as anaerobic exercise. The prior art systems of Sato described above relate to the combination of circulatory constriction and aerobic exercise.

OBJECTS OF THE INVENTION

A first object of this invention is a method for enhancing HGH generation in a human subject, the method having a first step of application of pressurized cuffs to subject extremities, the pressurized cuffs containing a circulating fluid at a reduced temperature compared to the temperature of human blood, the method having a second step of providing a fluid flow and pressure at a range between 33% and 220% of systolic blood pressure, a third step of subject ramp-up exertion for a duration of time until an equilibrium is reached in heart rate and blood pressure, a fourth step of repetitive intensive conditioning cycles, each conditioning cycle having repetitive sequences of intense high level exertion followed by low level exertion, and a fifth step of application of a reduced temperature flexible surface to a subject spine during a cooling down interval.

A second object of the invention is a method for enhanced oxygen transport to the brain following a vigorous exercise interval by cooling CSF in the spinal column through application of a flexible cooling pad to the spine of a subject in a horizontal position, the flexible pad having an elongate region carrying a circulated coolant having a first temperature and surrounded by a second region circulating a coolant having a higher temperature than the coolant of the elongate region, the elongate region preferably providing coupling to a subject spinal region.

SUMMARY OF THE INVENTION

The present invention is a method for enhancement of self-generated HGH in a human subject through the application of pressure and cooling to the limbs of the subject, in combination with physical exertion and monitoring of heart rate and systolic blood pressure. During a ramp-up interval, the subject engages in moderate exertion until a steady state blood pressure and heart rate is reached during the ramp-up phase, during which interval limb cuff pressure set to a pressure P which is in the range of 33% to 220% of systolic blood pressure. During one or more subsequent conditioning cycles, each conditioning cycle having a high rate of subject exertion followed by a comparatively lower rate of subject exertion, each conditioning cycle having an interval of intense exertion in a range of duration of one to four minutes followed by an interval of low exertion in a range of duration of one to four minutes. Three such cycles are provided, after which a cool-down cycle occurs. Following the cool-down cycle, the subject is placed in a horizontal position resting on a cooled spinal pad.

In another embodiment of the invention, a subject is placed in a horizontal position on a cooling pad following an interval of intense exercise, the cooling pad preferentially removing heat from the spine and thereby lowering the CSF temperature to improve delivery of CSF oxygen to the brain.

In another embodiment of the invention, the subject resting blood pressure is measured using pressure developed in a pressurized cuff, and the resting blood pressure is used in combination with a range such as 33% to 220% of this resting blood pressure to provide a pressurized cooling pressure which is later used during a pressurized cooling phase.

In another embodiment of the invention, a subject in a weightless environment with a series of pressurized cuffs, the pressures and temperatures of the cuffs sequenced to simulate walking or other exercise while in the weightless environment, thereby improving circulation through the veins.

In another embodiment of the invention, a subject in a weightless environment wears inflatable cuffs, and periodic pressures are to the cuffs in a sequence which provides for closure of venous valves to prevent retrograde blood flow and to improve circulation.

DETAILED DESCRIPTION OF THE INVENTION

Figure 1:
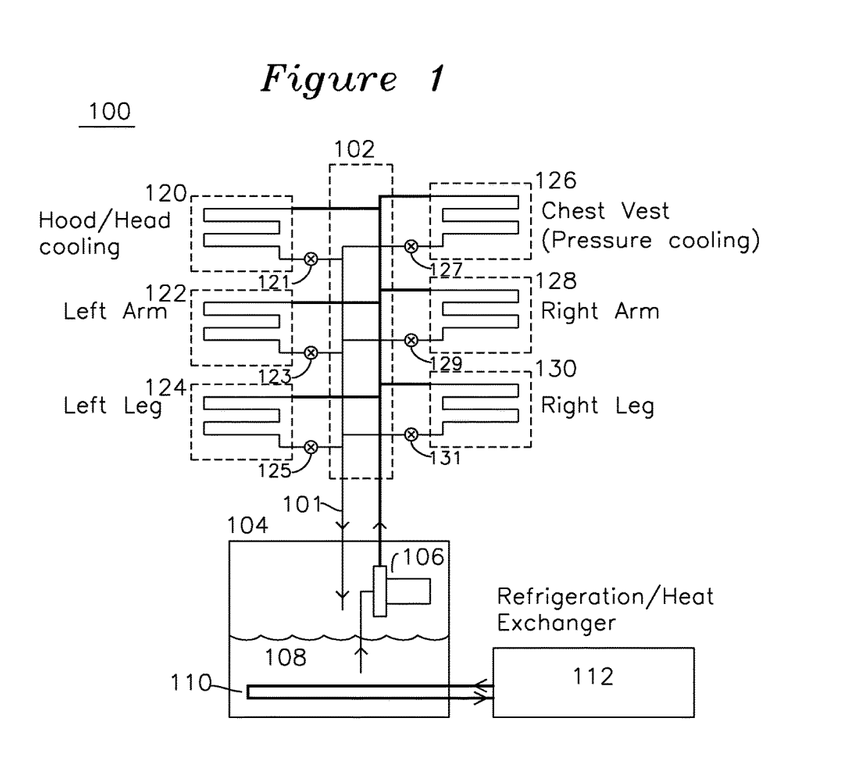
FIG. 1 shows a diagram for a core cooling system.

FIG. 1 shows a core cooling apparatus 100 for use with the present conditioning process. A reservoir 104 provides a cooled heat transfer fluid 108 such as water mixed with an anti-freeze such as ethlyene glycol or anti-bacterial or anti-fungal agent, the fluid 108 having a temperature regulated by refrigeration/heat exchanger unit 112 which may include refrigeration coil 110 for removing heat from fluid 108, with the refrigerator/heat exchanger 112 transferring removed heat energy to the external environment. Circulated coolant 108 which leaves reservoir 104 is preferentially in the temperature range of about 3.3 to about 15.5 degrees Celsius (38 to 60 degrees Fahrenheit), and the coolant 108 is circulated from pump 106 through a common manifold 102 to pressure/cooling cuffs 120, 122, 124, 126, 128, and 130, with pressures and flows controlled by regulation valves 121, 123, 125, 127, 129, and 131 respectively. Each independently controlled cuff provides pressure for reduction of blood circulation and reduced temperature for suppression of the evaporative cooling (sweating) response, with the fluid which leaves the cuff thereafter draining back to reservoir 104 such as through a return manifold 101. In particular, extremity cuffs 122, 124, 128, and 130 are used to provide a restriction in blood circulation in combination with cooling of blood in the associated limbs.

The application of pressure to subject limbs at a level sufficient to reduce circulation in combination with the use of a refrigerated coolant for removal of heat during physical exercise is referred to in the present patent application as "core cooling" or "pressurized core cooling". The applied cuff pressure P is typically a fraction of systolic blood pressure at a level sufficient to cause a "burning sensation" in subject muscles during exertion (as determined by the comfort level of the subject), but below the level of hypoxia or vascular occlusion, and the preferred core cooling pressure varies with systolic blood pressure, but is typically a fixed fraction of the systolic blood pressure in the range 33% to 220% as described earlier. The measurement of blood pressures may be incorporated into the blood pressure cuff through the addition of a microphone sensor and the use of the existing pressures developed in the cuff as part of the pressurized cooling.

In another preferred embodiment of the invention, a process for conditioning starts initially with reduced mechanical resistance during initial exercise, after which the level of exercise resistance (and associated exertion) is increased. After an initial ramp-up interval, during which blood pressure and heart rate reach equilibrium values (and the operating pressure P may be adjusted based on changes in physical parameters such as blood pressure), a series of conditioning cycles are performed, the conditioning cycles occurring in a group of one or more, each conditioning cycle having intense subject physical exertion lasting an interval of several minutes followed by a reduced level workout for an interval of several minutes, both the intense level and reduced level exertion being done with a relatively constant limb pressure applied, after which a rampdown interval occurs, followed by the application of core cooling without pressure such as by application of chilled coolant bladders to the spine and back, with preferential cooling applied to the elongate spinal region.

In one preferred embodiment of the invention, core cooling is applied during the cooling-off interval following exercise, which lowers the temperature of the spine, resulting in lower cerebral spinal fluid (CSF) temperature, and the reduced temperature CSF is capable of supporting a greater partial pressure of dissolved oxygen. The oxygen enhanced CSF is transported through the cooled areas of the spine and to the four ventricles of the brain such as by thermal convective circulation of the oxygen-enhanced CSF, thereby enhancing the level of oxygen provided to the brain.

The objective of core cooling is to optimize vascular performance by slowing down venous blood flow during an exercise interval lasting 20 minutes, or for a duration sufficient to cause the pooling of lactic acid in muscle tissue. Upon release of limb constriction after the conditioning cycles, the rapid release of pooled lactic acid provides stimulus to the subject's pituitary gland, which triggers additional HGH production. Over a human lifespan, HGH is produced by the body in comparatively high levels during the pre-teenage years when the body is functioning at a high metabolic rate compared to later years. The human body loses approximately 14% of its HGH production capability in each 10 year interval which follows the peak production years surrounding puberty. Measurements taken from healthy adults using the method and apparatus of the present invention indicate that HGH levels can be increased 300% above basal control levels through the effect of pooling lactic acid in muscle tissue through pressure cooling, which causes an enhanced pituitary gland response, with subsequent increased HGH generation compared to prior art systems. Recent measurements of HGH in subjects using the present pressure cooling apparatus and associated method of exercise indicate a 400% to 1200% increase in HGH when performing aerobic exercise in the core muscles and anaerobic exercise in the pressure-cooled extremities. It is believed that the combination of aerobic exercise with anaerobic pressure cooled extremities is the best mode of the invention for optimal generation of HGH.

The cooling method of the present apparatus and related process provides specific benefit in increasing the efficiency of HGH generation from vigorous exercise. During typical exercise, electro-chemical reactions which occur at the cellular level in the muscles cause heat generation, and the mechanism used in humans to reduce heat buildup is evaporative cooling at the skin surface which is experienced as body sweat. The perspiration cooling mechanism in humans results in blood being shunted from providing nutrients and oxygen to muscle tissue and instead the blood is used as a coolant to the skin instead of for nutrient transport to the muscle groups in exertion. As the subject exercises and core temperature rises, more blood gets shunted from deep muscle tissue with nutrient demand to the skin surface for body cooling. During intense exercise, up to 40 percent of the blood flow is shunted from exercising muscles to the skin surface for body cooling, and the reduction in capillary flow through the muscles is responsible for lactic acid burn experienced during exercise. In the present invention, advantageous pooling of lactic acid is provided by venous flow restriction, and the pooling of lactic acid during the ramp-up interval, and particularly during the conditioning cycles, is suddenly released at the end of the last conditioning cycle when the pressure cuffs are depressurized or removed. This sudden release causes the lactic acid to stimulate a pituitary gland response that is larger than without pressure cooling of the present invention because of the enhanced concentration of lactic acid being released. The simultaneous application of cooling with pressure keeps blood flow in the muscles, rather than shunting blood flow to the skin surface, resulting in maximum concentration of lactic acid and maximum pituitary gland response. Chemical reactions in the muscle tissue associated with muscle exertion also causes warming of the blood, the elevated blood temperature results in a reduction of oxygen transport since the elevated temperature causes a reduced hemoglobin oxygenation capacity. In contrast, conductive and convective surface cooling are experienced by a heavily exerting swimmer who has greater circulation through muscle and reduced loss of oxygen from elevated blood temperature. The advantageous cooling provided by swimming is offset by the disadvantage of the horizontal position during swimming exertion, which reduces the effect of the venous valves which provide protection against retrograde venous blood flow. Additionally, during exertion with the body in a vertical orientation, muscle forces related to the particular foot and leg movements associated with perambulation operate optimally on the venous blood valves located throughout the muscles of the thighs and legs, whereas the muscle groups associated with swimming and kicking in the water do not work as efficiently as those of walking on land. During exertion, the nearby muscle groups are operating on the vein walls and valves. When in an upright position, this results in a pumping action which pushes blood back to the heart through the venous one way valves which are located in muscle tissue, and the valve and muscle pumping action is optimal when the circulatory system is operating in an upright vertical position. With core cooling of the present invention, the reduction of core body temperature combined with pressure cooling of the extremities provides an increase in blood oxygen and a reduction in the shunting of blood away from muscle tissue as would be required for evaporative cooling from body sweat.

In another aspect of the invention, grounding of the body causes the release of serotonin responsible for deep sleep. Serotonin release also contributes to the generation of HGH. Grounding may be achieved by electrical connection of the subject to a reference voltage referred to as ground which is near to the subject, including a metal enclosure or structure such as an exercise machine operated by the subject, a surrounding enclosure such as a space capsule used for space travel, or in terrestrial use, the potential of earth which is adjacent to the subject.

Figure 1A:
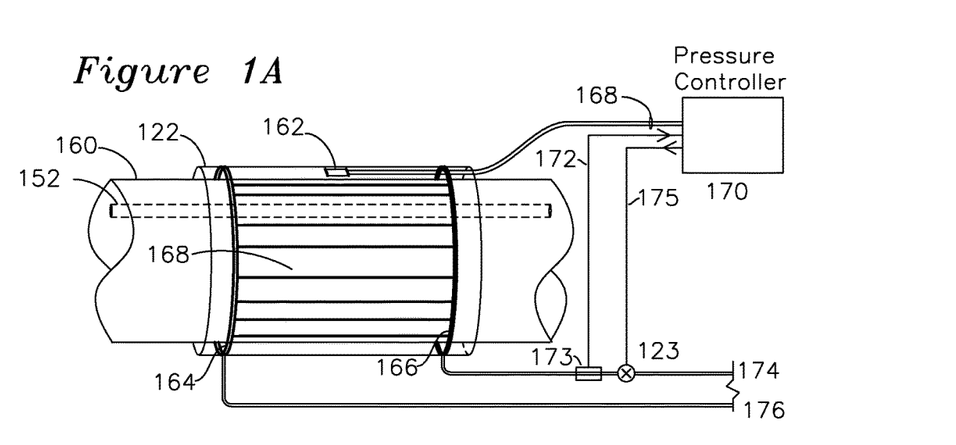
FIG. 1A shows a diagram of a subject extremity enclosed by the pressure cooling system of FIG. 1.

In an aspect of the invention shown in FIG. 1A, the pressure of each pressure cooling cuff 122, 124, 128, and 130 of FIG. 1 is individually set to an operational value P which is selected from the range of 33% TO 220% of systolic blood pressure, the operation of which is shown in detail for a particular cuff 122 enclosing an extremity 160. In operation, a subject arm 160 with a typical vein 152 is subject to elevated pressure with cooling from inlet 176 which pressure is coupled to cuff 122 manifold 164, passes through a plurality of flexible cuff passages 168 which expand and apply cooling and compressive pressure to veins 152 in subject arm 160, with the coolant collected in exit manifold 166 passing to regulation valve 123 and to outlet 174. The pressure controller 170 increases the pressure in the cuff 122 (using pressure controller output 175) by reducing flow in valve 123 until systolic blood flow is no longer detected using acoustic transducer 162 which is coupled to the subject's arm 160. Pressure controller 170 takes a measurement of pressure in the cuff 122 using pressure sensor 173 (and that is conveyed as pressure controller input 172 to the pressure controller) after valve 123 flow is reduced to eliminate detected flow using acoustic sensor 162. The operating pressure for therapeutic purposes is-then set to a fractional pressure P such as 33% to 220% of this systolic pressure by increasing flow in valve 123 until pressure detector 173 reports this same desired operating pressure. The blood pressure measurement process may be repeated at various intervals during the exercise cycle since blood pressure may vary during the course of the therapy. In a typical healthy patient at rest, the systolic blood pressure may be 120 mm Hg (2.32 psi), whereas during the ramp-up phase of exercise, the systolic blood pressure can reach 180 mm Hg (3.48 psi), and a conditioning cycle blood pressure may reach 190 mm Hg (3.7 psi) resulting in an operational cuff pressure P of 96 mm Hg (1.86 psi) at rest, and 144 mm Hg (2.78) during ramp-up exercise. The cuff pressure is tailored to each user based on the tradeoff between optimizing HGH generation with increased pressure and increased subject cooling versus optimizing patient comfort associated with reduced pressure or reduced cooling, which pressure and cooling parameters are also affected by subject exercise exertion level during the exercise and cool-down phases. In general, a wider cuff provides an improved comfort level for the user which translates into a longer exercise workout, as the discomfort of constricting pressure on a narrow section of a muscle group is reduced, and the addition of cooling in the pressure cuff provides an extended and more effective exercise interval by minimizing the HGH reduction caused when blood is shunted from the muscles to the capillaries at the skin surface and resulting in the generation of sweat at the skin surface. It is believed that a liquid pressurized and liquid cooled inflatable cuff which operates over the range of 20% to 80% of the length of the muscle group provides for improved comfort. This provides for a greatly improved duration of aerobic and anaerobic exercise than would be available using cuff pressure alone. Additionally, it is believed that the reduction in temperature of the blood in the limbs enables greater storage of oxygen in the blood, which enables extended muscle exertion, which generates an increased level of lactic acid, which triggers the generation of increased levels of HGH by the pituitary gland.

Figure 2A:
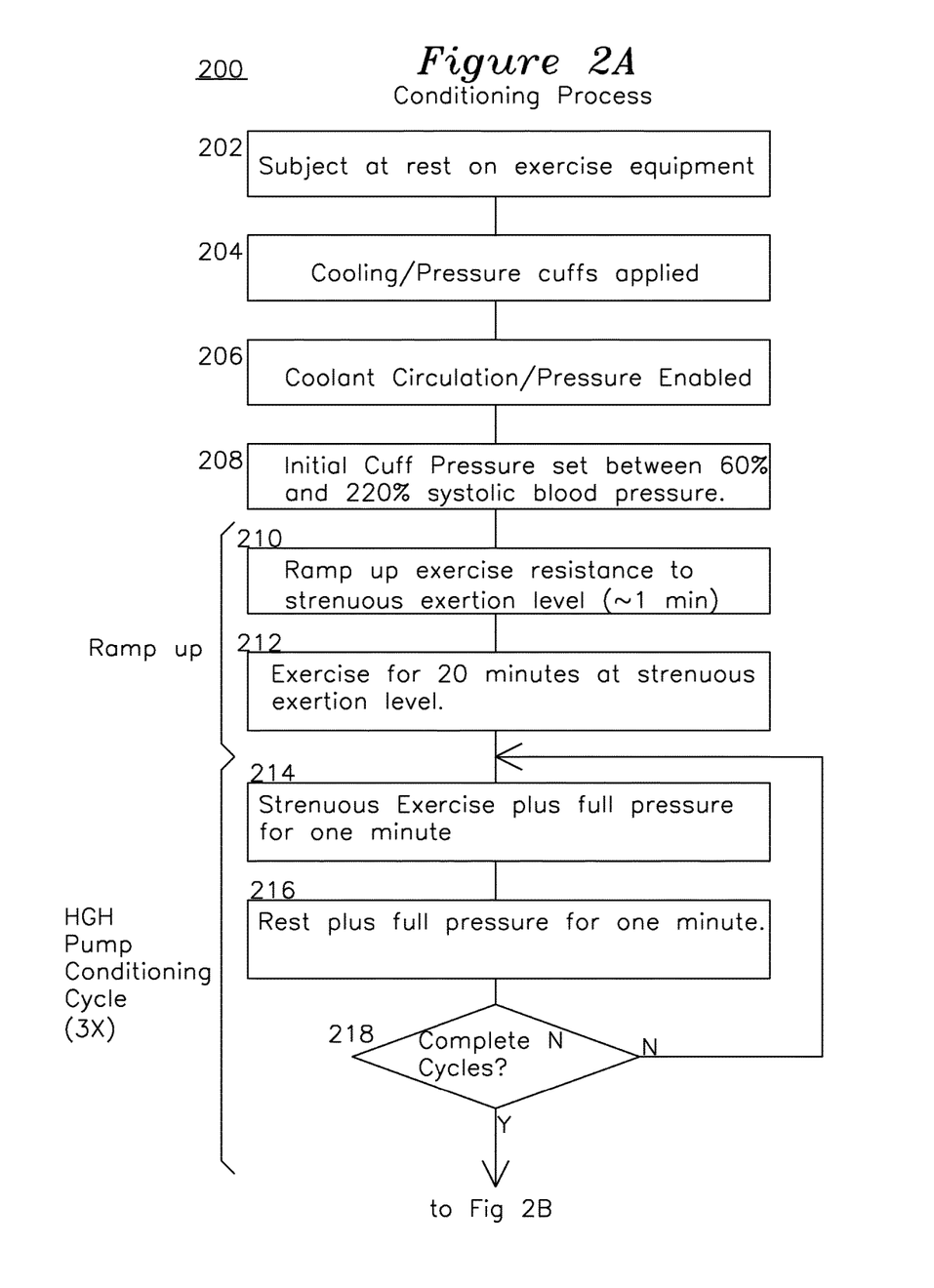
FIGS. 2A and 2B show a diagram for a conditioning process according to the present invention.
Figure 2B:
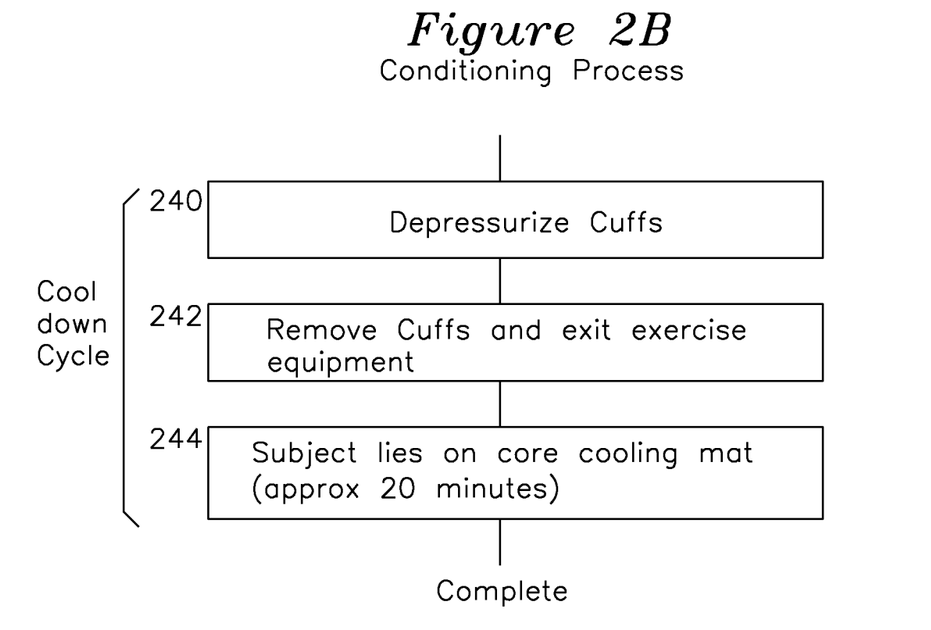

FIG. 2A shows a detailed view of the process 200 used in conjunction with the apparatus described in FIGS. 1 and 1A. A subject at rest enters the exercise equipment which is used in conjunction with pressure cooling in step 202, and has cooling pressure cuffs such as 120, 122, 124, 126, 128, 130 of FIG. 1 applied in step 204. Cuff pressure is applied such as by enabling circulation pump 106 and closing valves 121, 123, 125, 127, 129, or 131 of FIG. 1 in step 206, and during this interval, the systolic blood pressure may be measured on a per-cuff basis, or a single measurement made for application to all cuffs. The blood pressure measurement can be made at any time during the exercise regimen, preferably using the method described for FIG. 1A. In step 208, the operating cuff pressure is set to a threshold P derived from the systolic blood pressure as previously described. In step 210 and 212, the subject ramps up to a strenuous level of exercise and maintains this level for 20 minutes in step 212. During the ramp-up phase, the subject may adjust the individual cuff pressures for comfort, or they may be automatically re-computed as a fixed fraction of current systolic blood pressure for a new operational pressure P based on the systolic blood pressure measured as described in FIG. 1A. An HGH pump conditioning cycle is shown in steps 214, 216, 218, comprising strenuous exercise step 214 and reduced level of exercise 216, which is performed for a number N of cycles 218, depending on protocol. Three cycles (N=3) is a common conditioning cycle providing satisfactory results. Upon completion of the protocol, a cool down cycle occurs as shown in FIG. 2B comprising depressurization of cuffs such as by turning off circulation pump 106 or opening flow valves 121, 123, 125, 127, 129, and 131. The subject removes the depressurized cuffs in step 242 and thereafter lies 244 on a cooling mat for a cool down interval such as 20 minutes, where the subject is in a horizontal position with the cooling mat providing cooling to the spine, in particular to cool the CSF as was described earlier with the patient in a horizontal position. The interval of time spent in the horizontal position on the cooling mat 244 is determined by the amount of time required for the heart rate and blood pressure to return to resting levels, as shown in FIG. 3.

Figure 2C:
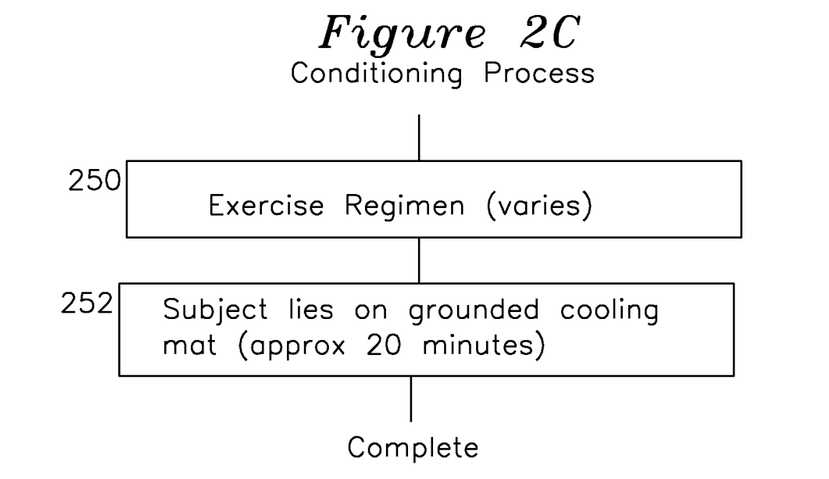
FIG. 2C shows a spinal cooling process for use with an exercise and conditioning process.

FIG. 2C shows the application of the beneficial CSF cooling to any exercise regimen, with or without pressure cooling of FIGS. 1 and 1A. In this application, the subject performs aerobic or anaerobic exercise for a duration of time typically in excess of 20 minutes, and thereafter lies on a grounded cooling mat which is coupled to the spine. In a preferred conditioning process, the subject lies on a grounded cooling mat, and in another embodiment of the invention, the cooling mat provides application of a cooling temperature such as about 3.3 to about 20 degrees Celsius (38 to 68 degrees Fahrenheit to a large surface area of the spine and surrounding tissues. In one embodiment of the invention, the spinal region is cooled to a constant first temperature such as 50 degrees Fahrenheit (from the range 38 to 68 degrees Fahrenheit), and the surrounding regions on either side of the spinal region are cooled to a slightly lower temperature that in the first temperature, and in a range such as about 3.3 to about 20 degrees Celsius (38 to 60 degrees Fahrenheit), additionally with a pulsating pressure having a cycle time in the range of 2 seconds, although it may be two or three times faster or slower than this nominal cycle time.

Figure 3:
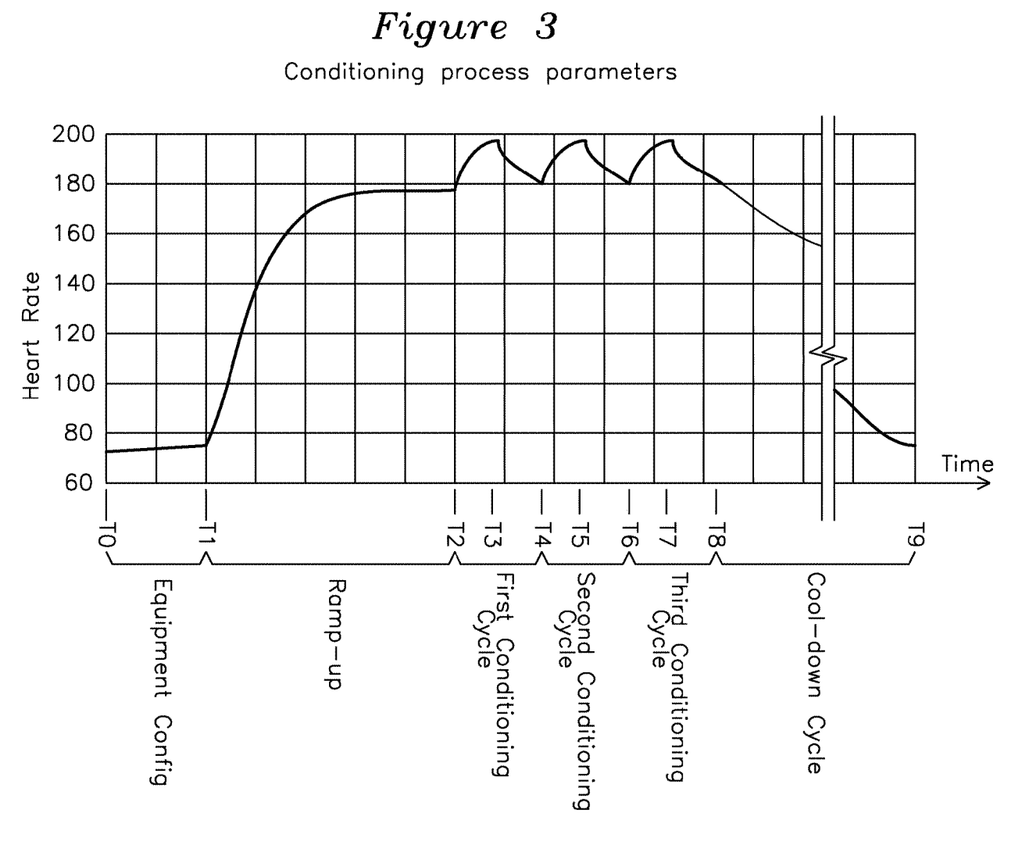
FIG. 3 shows a plot of physical parameters of heart rate and applied cuff pressure as measured in a subject through the conditioning process.

FIG. 3 shows a conditioning process with respect to heart rate. The subject is at a base heart rate of 70 beats per minute (bpm) during a first interval from T0 to T1, during which time the exercise machine equipment is being configured and pressure cuffs applied, as was described in steps 202, 204, 206 208 of FIG. 2. The ramp-up phase described in step 210 and 212 is shown during the interval from T1 to T2 (such as 20 minutes of exercise with the exercise machine set to moderate resistance) of FIG. 3, and the three repetitions of intense exertion (T2 to T3), such as provided by increased exercise resistance by the exercise machine, and decreased exertion (T3 to T4) such as by decreased exercise machine resistance are shown as a first conditioning cycle (T2 to T4), second conditioning cycle (T4 to T6), and third conditioning cycle (T6 to T8). The cool-down cycle is shown in the interval from T8 to T9.

Figure 4A:
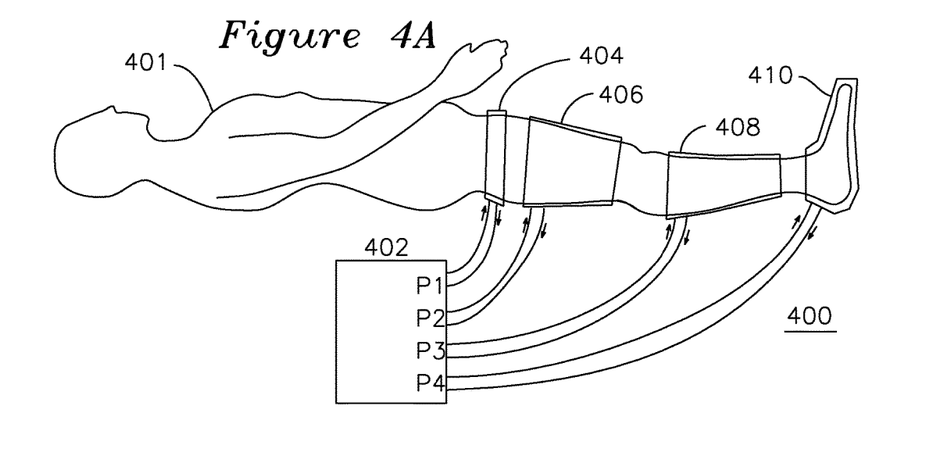
FIG. 4A shows pressure and cooling cuffs applied to an astronaut in space.
Figure 4B:
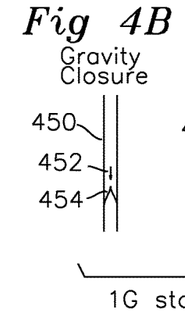
FIGS. 4B, 4C, 4D, 4E, and 4F are cross section views of a venous valve in a variety of different environmental conditions.
Figure 4C:
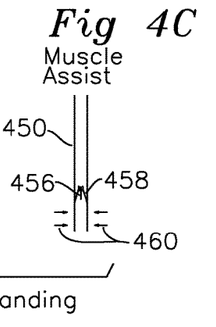
Figure 4D:
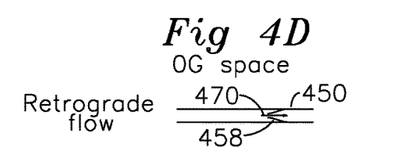
Figure 4E:
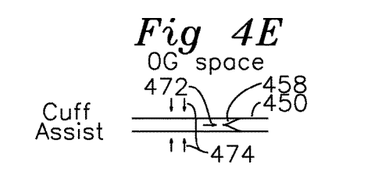
Figure 4F:
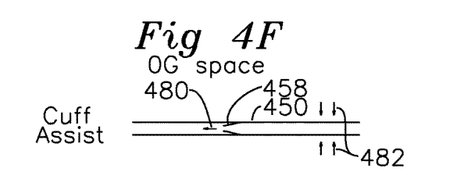

FIG. 4A shows an embodiment of the invention suitable for providing cooling and compression in a weightless environment, such as for use with a conditioning or exercise station for astronauts. One of the problems of space travel is the absence of gravity causes reduced muscle use and exertion, leading to muscle atrophy and loss of muscle tone. Additionally, the chronic absence of venous back-pressure in the extremities because of the absence of gravitational blood pressure cases the venous valves to remain fully or partially open, which causes retrograde and reduced venous blood flow. Under the influence of earth's gravity, the venous valves of the peripheral vascular system provide for enhanced circulation of blood as the muscle groups periodically compress the veins they enclose, thereby developing back-pressure in the venous valves and enhancing circulation by displacing blood during successive muscle contractions. The anatomical terms proximal and distal refer to the relative position of structures which are closer to the heart and further from the heart, respectively. Without the influence of earth's gravity, the gravitational blood pressure on the proximal side of the venous valve is eliminated, which causes the venous valves to remain partially open and for retrograde blood flow through the venous valve and venous system to occur. This reduced circulation rate in the lower extremities is a particular problem, where chronic exposure to the weightless environment can lead to compromised circulation and associated circulatory diseases over the long intervals of time associated with space travel. FIG. 4A shows a human subject 401 in a weightless environment with a vascular stimulation system 400 which includes a pressure/cooling controller 402, a gravity simulation cuff 404, a thigh cuff 406, calf cuff 408, and foot cuff 410. At least one of the cuffs 404, 406, 408, 410 is a pressure/cooling cuff, as was described for FIG. 1 and FIG. 1A. The controller 402 provides constant temperature coolant, and return valves control the pressure in each of P1, P2, P3, and P4 for the gravity stimulation cuff 402, thigh cuff 406, calf cuff 408, and foot cuff 410, respectively. FIGS. 4B and 4C show veins 450 in leg extremities in a 1 G environment where the upright gravity blood pressure 452 in vein 450 assists in the closure of venous valve 454. Muscle contractions in the muscles surrounding the flexible vein 450 result in compressive pressure 460 which overcomes this gravity blood pressure 452 of FIG. 4B and ejects blood 456 through the venous valve 458 during a phase when it opens in response to the muscle created back pressure 460, after which valve 458 closes as shown in FIG. 4B in response to the gravity back pressure. The repetitive application of muscle pressure 460 of FIG. 4C, such as from exercise, results in the repetitive cycle of venous valve 458 opening in response to muscle induced local blood pressure, and gravity induced blood pressure 452 causing venous valve 454 to close as shown in FIG. 4B. A problem of 0 G weightlessness in space with regard to venous valve operation is shown in FIGS. 4D and 4E. The same vein 450 does not have any applied gravity force and does not produce gravity blood pressure, which results in venous valve 458 remaining open, resulting in retrograde flow 470 as shown in FIG. 4D. The problem of retrograde blood flow in the extremities due to incomplete venous valve 470 closure is a significant long term risk in space flight, as delivery of blood through the circulatory system is compromised. The pressure cuffs of FIG. 4A can have controlled application of a sequence of pressure manipulated in a variety of methods which simulate the backpressure of gravity on the venous valves in a gravity environment, thereby providing enhanced venous return blood flow in weightless environments. FIG. 4D shows the effect of providing cuff pressure 474 in a dynamic manner to keep venous valve 458 closed during a first interval, and FIG. 4E shows a subsequent interval where distal muscle pressure 482 is applied, which either overcomes cuff pressure 474 shown in FIG. 4E, or alternatively the cuff pressure is reduced when exercise motion is detected or anticipated.

Figure 4G:
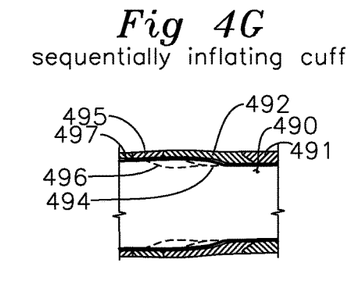
FIG. 4G shows a cross section view of a sequentially inflating cuff.

In another embodiment of the invention, each of the pressure cuffs 406, 408, 410 include a series of successively inflating chambers which provides a directed pressure, as shown in FIG. 4G. Limb 490 is surrounded by a pressurized cuff which has first inflating chamber 491 in a distal position, second inflating chamber 492, third inflating chamber 495 and fourth inflating chamber 497 in a proximal position, which may be achieved by interconnecting each chamber with a septum having an aperture for controlled inflation.

When first chamber 491 is pressurized, second chamber 492 inflates to the region shown by dashed line 494 and subsequently the third chamber inflates to the region shown by dashed line 496, thereby directing blood proximally. The operation of these cuffs as successively inflating may be used for any individual cuff 406, 408, or 410. In another embodiment of the invention, the arrangement of chambers in cuffs 406, 408, and 410 and the order of inflation may be used to simulate natural movements such as the changing foot pressure of walking in the case of cuff 410, or muscle contractions associated with walking, in the case of cuffs 406 and 410. Cuff 404 may operate independently for the singular purpose of creating an initial backpressure to close the venous valves, as shown in FIG. 4E. It is believed that the operating range for venous compression should be within 50% of a value which is 25% of the systolic blood pressure, and an appropriate range of pressurized cuff pressures would be 18-28 mm Hg (0.35-0.54 psi).

Figure 5:
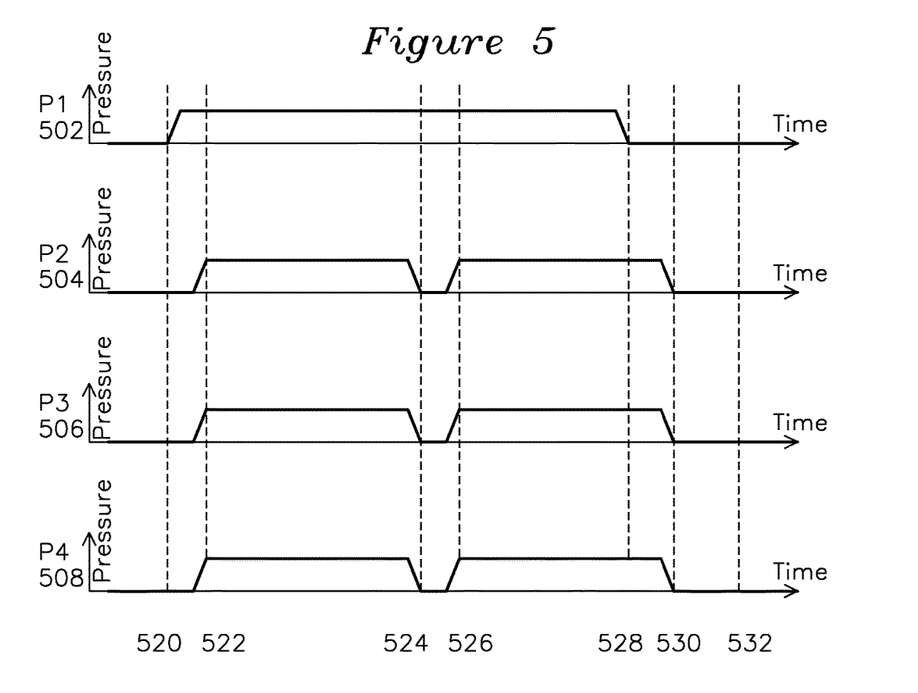
FIG. 5 shows a plot of applied cuff pressures over time which provide for enhanced blood flow in a zero gravity environment.

FIG. 5 shows one example of possible pressure profiles for each of the cuffs for use in a weightless environment. A single cycle is shown from start 520 to end 532, after which the cycle repeats at time 520. Gravity cuff 404 is pressurized P1 at time 520, during which time venous return pressure begins to build from interval 520 to 522. The other cuffs are pressurized from interval 522 to 524, released from 524 to 526, and then re-pressurized until time 528, when the gravity cuff P1 releases, and the pressure in cuffs P1, P2, P3 causes the blood to vigorously return to the heart. The pressure cuffs are released at time 530, and an interval of recovery 532 follows, after which the cycle starts again at time 520. In one embodiment of the invention, the cycle time from 520 to 532 is 30 seconds. In one embodiment of the invention for improving circulation in a weightless environment, a sequence of pressures is provided to cuffs 406, 408, 410 which simulates muscle contractions of walking, thereby improving blood flow. In another embodiment of the invention for improving circulation through the simulation of walking in a weightless environment, a sequence of pressures is provided to cuff 410, with a pressure first applied to the ball of the foot followed by a pressure to the heel of the foot. In another embodiment of the invention, a sequence of cuff pressure is applied to cuffs 404, 406, 408, and 410 which improves blood flow in a weightless environment by assisting in the closure of the distal venous valves from cuff 404 by the short application of pressure in cuffs 404, 406, 408, 410 which closes the venous valves in the manner shown in FIG. 4E. In another embodiment of the invention, a first sequence of pressures is provided which directs venous blood proximal from the limb and towards the heart, and a second sequence of pressures is provided which subsequently closes the venous valves preventing venous distal retrograde flow.

In one embodiment of the invention for HGH generation triggered by lactic acid from anaerobic exercise, the pressurized and cooled cuffs carry a cooled liquid having a temperature which is dynamically adjusted to provide optimal vasoconstriction (temperature-induced reduction in the diameter of the veins). A level of temperature-associated vasoconstriction of the veins during exercise is desired at a level which is sufficient to reduce oxygen delivery to the muscles during exercise to signal a request for the generation of HGH through muscle lactic acid release. However, an excessive level of vasoconstriction may result in muscle cramping, temperature related discomfort, or hypothermia induced by the removal of heat in excess of its generation in the muscles. Optimal control of vasoconstriction may be achieved by dynamically adjusting the coolant temperature to maintain a threshold or a particular level of distal pulse (measurement of pulse taken at a finger or toe) or in conjunction with a blood pressure measurement to maintain a particular parametric vasoconstriction value, where an increase in vasoconstriction is indicated by either a decreased distal pulse, or a reduction in distal blood pressure. In one embodiment of the invention, the coolant is operated in the low temperature range of about 8.9 to about 20 degrees Celsius (38° F. to 48° F.) for patients with a high body mass, and in another embodiment of the invention, the coolant is operated in the range of about 8.9 to about 20 degrees Celsius (48° F. to 68° F.) for patients with a low body mass. In another embodiment of the invention, the temperature of the coolant applied at constant pressure to the cuffs is temporally varied, with the coolant starting at a comparatively low end of the temperature range during an interval of high exertion, as measured by the output of an exercise machine (not shown), or other external measurement of exertion, and the coolant temperature is increased during an interval of reduced exertion. In another embodiment of the invention, the previously described coolant temporal temperature change is applied either prior to or after the change in exertion to achieve either improved comfort or improved HGH generation. In another embodiment of the invention, the extremity pressurized cooled cuffs of FIG. 4 operate in conjunction with exercise equipment (not shown) such that the extremity cuff generates backpressure is determined by the timing and coordination of FIG. 5.

Figure 6:
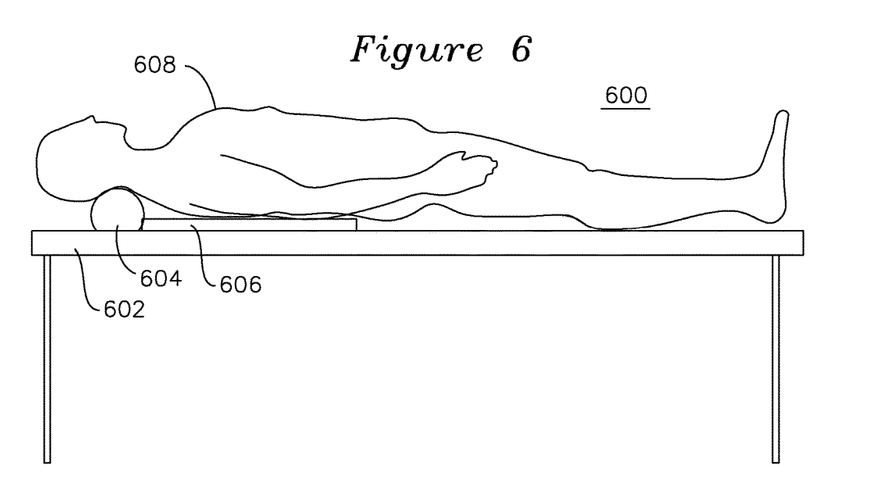
FIG. 6 shows the diagram of a cooling mat in contact with a user.
Figure 7:
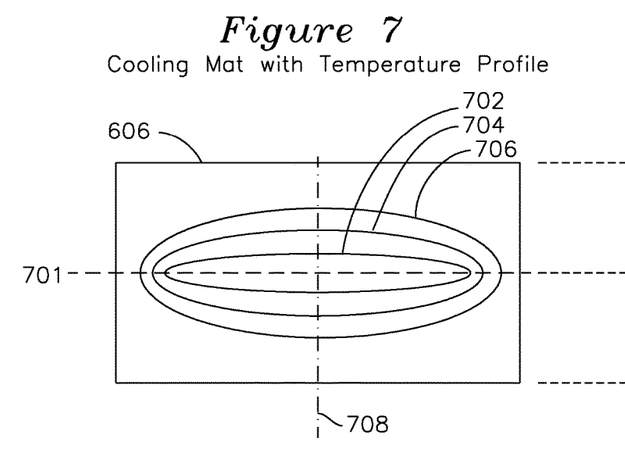
FIG. 7 shows isoplanar temperature plot of the cooling mat of FIG. 6.
Figure 7A:
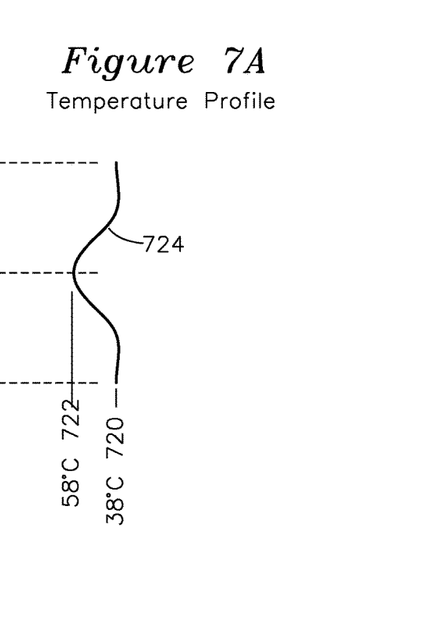
FIG. 7A shows the cross section view of the temperature profile of FIG. 7.

FIG. 6 shows another embodiment of the invention as a cooling mat 606 with headrest 604 placed upon a support surface such as a table 602 for a cooling system 600. FIG. 7 shows a plan view of mat 606, which has a series of chilled water cooling channels which create elongate isothermal profiles 702, 704, and 706 along a major axis 701 with a thermal gradient such that inner channel 702 has the highest temperature and outer channel 706 has the lowest temperature. This is shown such as through section 708 shown in the corresponding temperature profile 724 of FIG. 7A, such that the inner elongate region may have a temperature with a maximum of about 20° C. (68° F.) 722, and the outer region may have a temperature with a minimum of about 3.3° C. (38° F.) 720. Mat 606 may be constructed of a series of bladders with restricted flow such that the coldest cooling water circulates through inner bladders in region 702, and circulates successively to outer region 706, with the flow rate of the cooling water selected to achieve the desired temperature profile such as shown in FIG. 7A. Alternatively, the cooling mat 606 may achieve the cooling profile shown in FIG. 7A through the unrestricted flow of coolant through channels which match the profile shown in FIG. 7, with a first channel 702 having an inlet and outlet on opposite ends of the major axis 701, and the other coolant channels 704 and 706 circulating coolant with decreased temperature, as required by the desired temperature profile shown in FIG. 7A. It is believed that the coolant temperatures should be within the range of about 3.3° C. to about 14.4° C. (38-58° F.), with the coolant closest to the spinal column in channel 702 at an elevated temperature compared to the muscular regions on either side of the spine in regions 704 and 706.

The description of the embodiments of the invention are not intended to limit the scope of the invention, but to illustrate a particular best mode of operation of the invention. The steps of the invention can be practiced in combination or separately without loss of benefit. In particular, the operational pressure may be set to a fixed threshold or an adjustable threshold, and the measurement of systolic blood pressure may be performed once or over several iterations during the exercise cycle.

I claim:

1. A physical conditioning process comprising:
   pressurizing one or more extremities of a subject to produce one or more pressurized extremities;
   cooling one or more of said cooled-pressurized extremities to produce one or more cooled-pressurized extremities;
   exercising one or more of said pressurized extremities of said subject to produce one or more treated extremities, said exercising including one or more cycles of a duration of high exertion followed by a duration of comparatively low exertion; and
   adjusting said pressure to one or more of said treated extremities during one or more of said exercising intervals based on maintaining 33-220% of a systolic blood pressure, and also changing said cooling to provide greater cooling during said intervals of high exertion and comparatively less cooling during said intervals of comparatively low exertion;
   the pressure and an exercise resistance during the duration of high exertion and low exertion selected to cause a rapid release of lactic acid upon release of pressure after the one or more cycles, the rapid release of lactic acid sufficient to stimulate an enhanced pituitary gland response of the subject, the enhanced pituitary gland response resulting in a release in the range of 400-1200% of human growth hormone in the subject.

2. The physical conditioning process of claim 1, wherein said subject is a human.

3. The physical conditioning process of claim 1, wherein said extremities include legs.

4. The physical conditioning process of claim 1, wherein said extremities includes arms.

5. The physical conditioning process of claim 1, wherein one or more pressurizable cuffs pressurizes one or more of said extremities to produce one or more of said pressurized extremities.

6. The physical conditioning process of claim 5, wherein a transducer positioned on one or more of said pressurizable cuffs allows a measurement of systolic blood pressure.

7. The physical conditioning process of claim 1, wherein cooling one or more of said pressurized extremities includes transferring heat from one or more of said pressurized extremities to a coolant having a temperature between 38 degrees Fahrenheit and 68 degrees Fahrenheit.

8. The physical conditioning process of claim 7, wherein said coolant is delivered to one or more of said pressurizable cuffs.

9. The physical conditioning process of claim 1, further comprising placing said subject in a substantially horizontal position and cooling the spine and surrounding surface area of said human subject after exercising one or more of said cooled-pressurized extremities of said subject.

10. The physical conditioning process of claim 1, wherein at each of one or more of said intervals, said pressure of one or more extremities of said subject is adjusted to a value between 33% and 220% of said measured blood pressure.

11. A physical conditioning process comprising:
    pressurizing one or more extremities of a subject to produce one or more pressurized extremities;
    cooling one or more of said pressurized extremities by transferring heat from one or more of said pressurized extremities to a coolant to produce one or more cooled-pressurized extremities;
    exercising one or more of said cooled-pressurized extremities of said subject to produce one or more treated extremities and measuring a blood pressure or a heart rate of said subject at one or more exercising intervals to obtain a measured blood pressure or a measured heart rate associated with one or more of said exercising intervals; and
    adjusting a temperature of said coolant during one or more of said exercising intervals based on said measured blood pressure or said heart rate associated with one or more of said exercising intervals;
    said exercising including conditioning cycles of high and low applied pressure, and after the final conditioning cycle, suddenly releasing the pressure of said cuffs for providing a release of lactic acid in exercised muscles of said subject wearing said cuffs;
    an exertion level during the exercising intervals selected such that the rapid release of lactic acid is sufficient to stimulate an enhanced pituitary gland response of the subject, the enhanced pituitary gland response resulting in the release of increased human growth hormone in the subject in the range of 400-1200%.

12. The physical conditioning process of claim 11, wherein said subject is a human.

13. The physical conditioning process of claim 11, wherein said coolant has a temperature between 38 degrees Fahrenheit and 68 degrees Fahrenheit.

14. The physical conditioning process of claim 11, wherein one or more pressurizable cuffs pressurizes one or more of said extremities to produce one or more of said pressurized extremities.

15. The physical conditioning process of claim 11, further comprising placing said subject in a substantially horizontal position and cooling the spine and surrounding surface area of said human subject after exercising one or more of said cooled-pressurized extremities of said subject.

16. A physical conditioning process comprising:
    applying one or more cuffs to one or more extremities of a subject to produce one or more pressurizable cuffs, wherein said pressurizable cuffs have a long axis length sufficient to wrap around and enclose an extremity and a short axis width sufficient to extend across between 20% and 80% of a length of a muscle group of one or more of said extremities;
    pressurizing one or more of said pressurizable cuffs to produce one or more pressurized extremities, said pressurizing sufficient to reduce blood flow in an associated said pressurized extremity;
    cooling one or more of said pressurized extremities to produce one or more cooled-pressurized extremities, said cooling sufficient to produce vasoconstriction in an extremity; and
    exercising said cooled-pressurized extremities of said subject in a series of cycles, each said cycle providing high exercise resistance during a first duration and a comparatively lower exercise resistance during a second duration;
    the pressure of the one or more cuffs, the high exercise resistance, and the lower exercise resistance selected to cause a rapid release of lactic acid upon release of pressure, the rapid release of lactic acid sufficient to stimulate an enhanced pituitary gland response of the subject, the enhanced pituitary gland response resulting in the release of increased human growth hormone of 400% to 1200% in the subject;
    the subject thereafter laying on a cooling mat having a low temperature central elongate region providing cooling to a spinal region, the cooling mat having a comparatively higher temperature in regions other than said central elongate region;

said comparatively higher temperature selected to be lower than a subject core temperature and in a range sufficient to cause a greater partial pressure of dissolved oxygen in a cerebral spinal fluid (CSF) of the subject laying on the cooling mat.

17. The process of claim 16, wherein said subject is a human.

18. The process of claim 17, wherein said cooling is provided by a fluid circulated through said one or more pressurizable cuffs, said fluid temperature is adjusted to have a temperature in the range of 38 degrees Fahrenheit to 48 degrees Fahrenheit for a subject with high body mass and a temperature range of 48 degrees Fahrenheit to 68 degrees Fahrenheit for a subject with comparatively lower body mass.

19. The process of claim 17, wherein said series of cycles is preceded by a ramp-up period following a period of moderate exercise resistance to increased exercise resistance of said series of cycles.

20. The physical conditioning process of claim 17, wherein one or more of said pressurizable cuffs are pressurized between 33% and 220% of a systolic blood pressure of said subject at rest.

21. The process of claim 17, further comprising placing said subject on said cooling mat in a substantially horizontal position to cool the core of said subject's body.

22. The process of claim 21, wherein said cooling mat includes a liquid cooled flexible bladder.

* * * * *